(12) United States Patent
Sheeran et al.

(10) Patent No.: US 6,194,569 B1
(45) Date of Patent: Feb. 27, 2001

(54) EFFICIENT PROCESS FOR THE PREPARATION OF [S-(R,S)]-N-[1,3-BENZODIOXOL-5-YL)BUTYL]-3,3-DIETHYL-2[4-[4-METHYL-1-PIPERAZINYL)CARBONYL]PHENOXY]-4-OXO-1-AZETIDINE CARBOXAMIDE, A HUMAN LEUKOCYTE ELASTASE INHIBITOR

(75) Inventors: Patrick J. Sheeran, Landenberg; Luigi Anzalone, West Chester, both of PA (US); Hui-Yin Li, Hockessin, DE (US); Joseph M. Fortunak, Newark, DE (US); Louis Storace, Middletown, DE (US)

(73) Assignee: DuPont Pharmaceuticals Company, Wilmington, DE (US)

( * ) Notice: Subject to any disclaimer, the term of this patent is extended or adjusted under 35 U.S.C. 154(b) by 0 days.

(21) Appl. No.: 09/385,271

(22) Filed: Aug. 30, 1999

Related U.S. Application Data

(60) Provisional application No. 60/098,510, filed on Aug. 31, 1998.

(51) Int. Cl.[7] ................ C07D 403/12; C07D 405/14
(52) U.S. Cl. ............................................................. 540/360
(58) Field of Search ............................................... 540/360

(56) References Cited

U.S. PATENT DOCUMENTS

| | | | |
|---|---|---|---|
| 5,149,838 | 9/1992 | Humphrey et al. | 549/471 |
| 5,229,381 | 7/1993 | Doherty et al. | 514/210 |
| 5,591,737 | 1/1997 | Doherty et al. | 514/210 |

FOREIGN PATENT DOCUMENTS

| | | |
|---|---|---|
| 9716448 | 5/1997 | (WO) . |
| 9734887 | 9/1997 | (WO) . |

OTHER PUBLICATIONS

Nowick et al., J. Org. Chem., 1992, 57, pp. 7364–7366.
Shah et al., J. Med. Chem., 1992, 35 (21), pp.3745–3754.
MacDonald et al., J. of Med. Chem., vol. 41, No. 21 (1998), pp. 3919–3922.

Cvetovich et al., J. of Org. Chem., vol. 61, No. 19 (1996), pp. 6575–6580.

*Primary Examiner*—Mark L. Berch
*Assistant Examiner*—Thomas McKenzie

(57) ABSTRACT

Processes for the preparation of [S-(R,S)]-N-[1,3-benzodioxol-5-yl)butyl]-3,3-diethyl-2[4-[4-methyl-1-piperazinyl)carbonyl]phenoxy]-4-oxo-1-azetidine carboxamide, a useful inhibitor of human leukocyte elastase (HLE), are described. The process including (a) contacting a compound of formula (II):

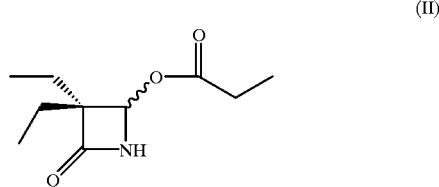

(II)

with a compound of formula (III):

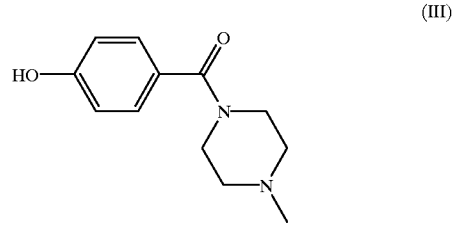

(III)

in a first polar solvent system in the presence of an aqueous base and a phase transfer catalyst, to form the title compound, or a salt form thereof.

12 Claims, No Drawings

EFFICIENT PROCESS FOR THE PREPARATION OF [S-(R,S)]-N-[1,3-BENZODIOXOL-5-YL)BUTYL]-3,3-DIETHYL-2[4-[4-METHYL-1-PIPERAZINYL) CARBONYL]PHENOXY]-4-OXO-1-AZETIDINE CARBOXAMIDE, A HUMAN LEUKOCYTE ELASTASE INHIBITOR

This application claims the benefit of U.S. Provisional Application No. 60/098,510, filed Aug. 31, 1998.

FIELD OF THE INVENTION

The present invention relates generally to an efficient and practical synthesis of [S-(R,S)]-N-[1,3-benzodioxol-5-yl) butyl]-3,3-diethyl-2[4-[4-methyl-1-piperazinyl)carbonyl] phenoxy]-4-oxo-1-azetidine carboxamide. This compound is an inhibitor of human leukocyte elastase (HLE) and useful for the treatment of abnormalities such as cystic fibrosis, acute respiratory distress syndrome, chronic bronchritis and other immuno response disorders.

BACKGROUND

Human leukocyte elastase (HLE) is a serine protease present in the azurophilic granules of human polymorphonuclear leukocytes. In the intracellular environment, HLE is capable of degrading a variety of structural proteins, including elastin and collagen. The destructive power of HLE is controlled by its natural inhibitors, but in diseases such as emphysema, cystic fibrosis and rheumatoid arthiritis, it is believed that the balance between HLE and its inhibitor is disrupted and the unbound HLE causes destruction of connective tissue.

U.S. Pat. No. 5,229,381 indicates the value of the compound of formula (I) as an effective inhibitor of human leukocyte elastase.

(I)

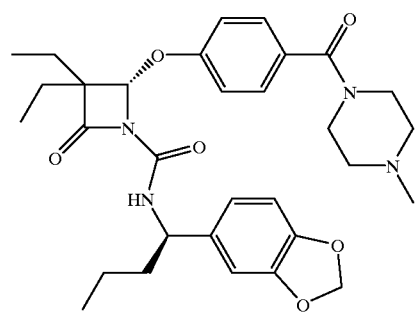

International publication WO 97/16448 describes a general synthesis of (I) which involves the displacement of the propionate group of 3,3-diethyl-4-(propionyloxy)-2-azetidinone by benzyl 4-hydroxybenzoate (benzyl paraben) to give the desired 3,3-diethyl-4-[(4'-benzyloxycarbonyl) phenoxy]-2-azetidinone.

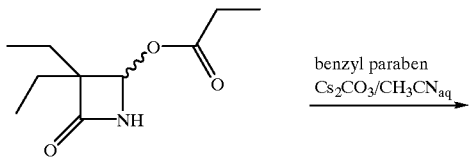

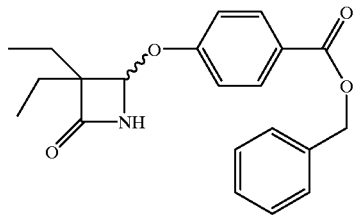

The racemic ester is converted to the racemic carboxylic acid by transfer hydrogenolysis, and the (S) enantiomer obtained by precipitating the undesired salt with (R)-a-methylbenzyl amine. The desired 3-(S) acid is then isolated from the filtrate by adding (S)-a-methyl benzyl amine (S-MBA) and filtering the solid S,S-MBA salt. The chiral purity is typically brought to an acceptable level by recrystallization, and the purified 3-(S)-acid liberated from the salt by the addition of acid.

The subsequent coupling with N-methyl piperazine is accomplished through the use of dicyclohexylcarbodiimide and hydroxybenzotriazole to give the key S-azetidinone intermediate (IV-b).

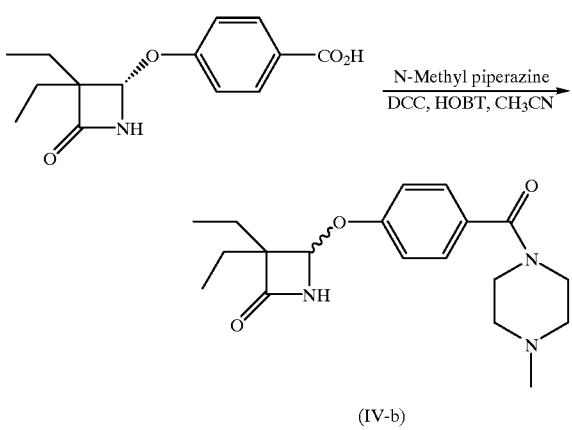

(IV-b)

The S-azetidinone (IV-b) is ultimately condensed with the appropriate R-isocyanate in the presence of a catalytic amount of a weak base such as 1,8-diazabicyclo[5.4.0] undec-7-ene (DBU) to give the desired [S-(R,S)]-N-[1,3-benzodioxol-5-yl)butyl]-3,3-diethyl-2[4-[4-methyl-1-piperazinyl)carbonyl]phenoxy]-4-oxo-1-azetidine carboxamide (I).

The utility of the present invention lies in the discovery of an efficient process which permits a more favorable commercial manufacture of (I). Reaction of the β-lactam 3,3-diethyl-4-propionyloxy-2-azetidinone directly with 1-(4-hydroxybenzoyl)-4-methylpiperazine provides the racemic (R,S)-1-[4-[(3,3-diethyl-4-oxo-2-azetidinyl) oxy]benzoyl]-4-methylpiperazine. The resolution of the racemate is achieved through the formation of the 2,3:4,6-Di-O-isopropylidene-2-L-gulonic acid (DAG) salt of the undesired (R)-isomer, which precipitates under proper conditions. The desired (S)-isomer (IV-b) is recovered from the reaction liquors by the addition of an antisolvent. The resolution of this intermediate obviates the need for a carboxylic acid for salt formation, thus avoiding the use of harmful and expensive reagents such as dicyclohexyl-carbodiimide and hydroxybenzotriazole in favor or a shorter synthetic route.

The desired (S) β-lactam (IV-b) is isolated from the filtrate in high chemical yield and enantiomeric purity. The recovered (R) β-lactam/DAG salt may be racemized back to (S,R) β-lactam to optimize yield of the (S)-isomer, and the DAG recovered from an aqueous stream by controlled acidification. Overall, the process allows for maximum yield of an advanced intermediate in addition to cost saving recovery of the resolving agent.

The product of the resolution is condensed with (R)-5-(1-isocyanatobutyl)-1-3-benzodioxole to give (I) under conditions which offer advantages over previously reported procedures. Specifically, the present invention describes the use of a catalytic amount of strong base, which minimizes degradation by enhancing reaction rate.

The present invention further describes a unique phosgenation protocol for the preparation of an isocyanate from (R)-a-propyl-piperonylamine. The process minimizes epimerization resulting from trace amounts of iron found to be a common contaminant in commercial phosgene. This discovery also allows for isocyanate formation in iron equipment which would otherwise be a likely source of dissolved iron. Such flexibilty ultimately allows for significant cost reduction and versatility in the commercial manufacture of (I).

SUMMARY OF THE INVENTION

The present invention relates generally to processes for the efficient production of [S-(R,S)]-N-[1,3-benzodioxol-5-yl)butyl]-3,3-diethyl-2[4-[4-methyl-1-piperazinyl)carbonyl]phenoxy]-4-oxo-1-azetidine carboxamide (I):

(I)

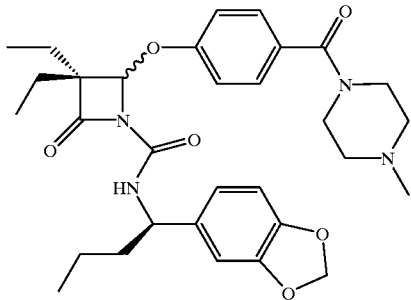

which has been achieved by the inventors' discovery that a compound of formula (I) or a pharmaceutically acceptable salt form thereof, is formed by a high yielding process, comprising the reactions:

(1) contacting a compound of formula (II):

(II)

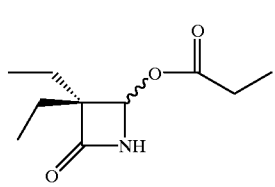

with a compound of formula (III):

(III)

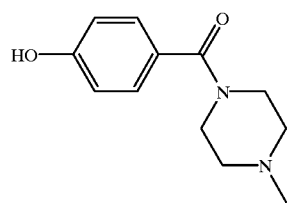

in a polar solvent system, in the presence of an aqueous base and a phase transfer catalyst to form a compound of formula (IV):

(IV)

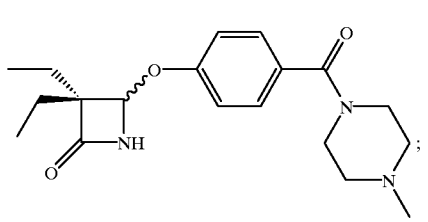

(2) contacting the compound of formula (IV) with 2,3:4,6-Di-O-isopropylidene-2-keto-L-gulonic acid (DAG) in a suitable solvent to form a precipitate of formula (IV-a):

(IV-a)

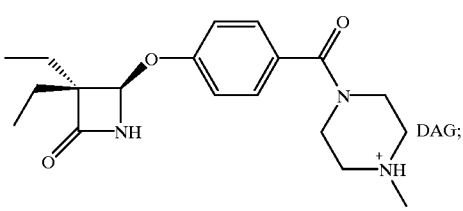

and a mother liquor containing a compound formula (IV-b):

(IV-b)

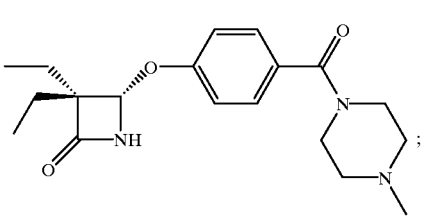

and contacting the mother liquor with an antisolvent to precipitate the compound of formula (IV-b) as a crystalline solid;

(3) racemizing the free base of the compound of formula (IV-a), as necessary, to form a compound of formula (IV) and repeating reaction (2);

(4) contacting a compound of formula (V):

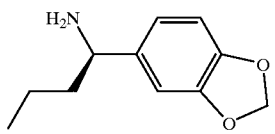
(V)

or a salt form thereof, with phosgene or an equivalent thereof, in a suitable solvent, at a suitable temperature in the presence of a catalytic amount of a complexing agent to form a compound of formula (VI):

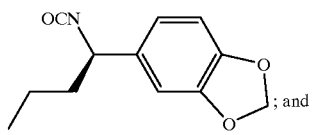
(VI)

(5) contacting the compound of formula (IV-b) with the compound of formula (VI), at a suitable temperature, in the presence of a catalytic amount of a strong base to form a compound of formula (I), or a pharmaceutically acceptable salt form thereof.

DETAILED DESCRIPTION OF THE INVENTION

Thus, in a first embodiment, the present invention provides a process for the preparation of compounds of formula (IV):

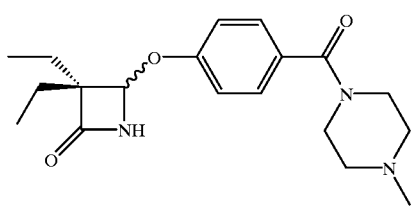
(IV)

or a salt form thereof; the process comprising:

(a) contacting a compound of formula (II):

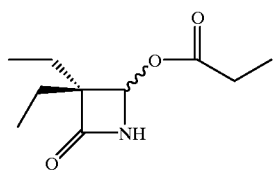
(II)

with a compound of formula (III):

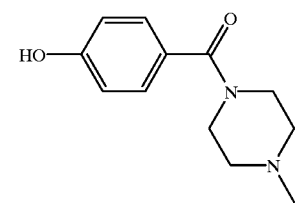
(III)

in a polar solvent system in the presence of an aqueous base and a phase transfer catalyst, to form a compound of formula (IV), or a salt form thereof.

In a preferred embodiment, in reaction (a):

the first polar solvent system comprises a mixture of water and a cosolvent selected from:
isopropyl acetate, methyl acetate, ethyl acetate, tert-butyl acetate, toluene, and tert-butyl methyl ether;

the aqueous base is selected from:
lithium carbonate, sodium carbonate, potassium carbonate, and cesium carbonate; and the phase transfer catalyst is selected from:
tetrabutylammonium bromide, tetrabutylammonium iodide, tetrabutylammonium hydrogen sulfate, and tetrabutylammonium chloride.

In a second embodiment, the present invention describes a process for the preparation of a compound of formula (IV-b):

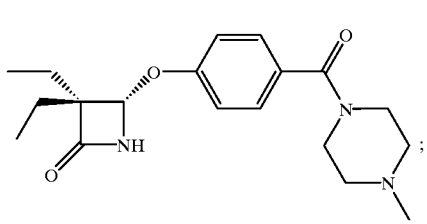
(IV-b)

the process comprising:

(b) contacting a compound of formula (IV):

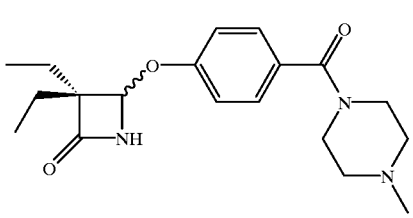
(IV)

with 2,3:4,6-Di-O-isopropylidene-2-keto-L-gulonic acid in a suitable solvent to precipitate a compound of formula (IV-a):

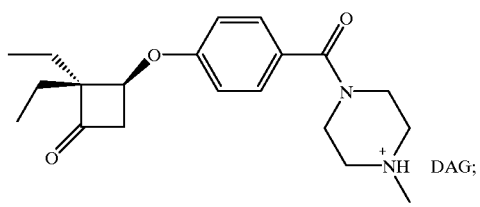

(IV-a)

and a mother liquor containing the compound of formula (IV-b);
  (c) isolating the mother liquor; and
  (d) contacting the mother liquor with an antisolvent to precipitate a compound of formula (IV-b) as a crystalline solid.

In a preferred embodiment, the suitable solvent in (b) is selected from:
  isopropyl acetate, methyl acetate, ethyl acetate, tert-butyl acetate, and acetone;
isolating in (c) comprises filtering; and
the antisolvent in (d) is selected from:
  pentane, heptane, hexane, diethyl ether, and tert-butyl methyl ether.

In another preferred embodiment, the process of (b)–(d) further comprises:
  (d-i) free-basing and racemizing the compound formula (IV-a) to form a compound of formula (IV);
  (d-ii) contacting the compound of formula (IV) formed in (d-i) with 2,3:4,6-Di-O-isopropylidene-2-keto-L-gulonic acid in a second suitable solvent to precipitate a second crop of a compound of formula (IV-a), and a second mother liquor containing a compound of formula (IV-b);
  (d-iii) isolating the second mother liquor; and
  (d-iv) contacting the second mother liquor with a second antisolvent to precipitate a second crop of a compound of formula (IV-b) as a crystalline solid.

In a more preferred embodiment, free-basing and racemizing in (d-i) comprises contacting the compound of formula (IV-a) with an aqueous base in a polar solvent system comprising an aqueous phase and a cosolvent, in the presence of a phase transfer catalyst.

In an even more preferred embodiment, the aqueous base is selected from:
  lithium carbonate, sodium carbonate, potassium carbonate, and cesium carbonate;
the cosolvent selected from:
  ethyl acetate, toluene, acetonitrile, isopropyl acetate, and methyl acetate; and
the phase transfer catalyst is selected from:
  tetrabutylammonium bromide, tetrabutylammonium chloride, tetrabutylammonium iodide, and tetrabutylammonium hydrogen sulfate.

In another even more preferred embodiment, wherein racemizing the free base in (d-i) comprises contacting the compound of formula (IV-a) with an aqueous base in a solvent system comprising an aqueous phase and a cosolvent in the presence of a phase transfer catalyst, the process further comprises:
  (d-v) isolating the aqueous phase;
  (d-vi) precipitating DAG monohydrate by contacting the aqueous phase with an aqueous acid; and
  (d-vii) isolating the DAG monohydrate.

In another preferred embodiment, the process further comprises:

(e) contacting the compound of formula (IV-b) with a compound of formula (VI):

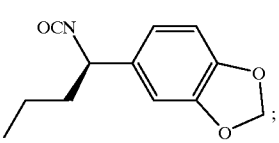

(VI)

in a coupling solvent, in the presence of a catalytic amount of a strong base to form a compound of formula (I):

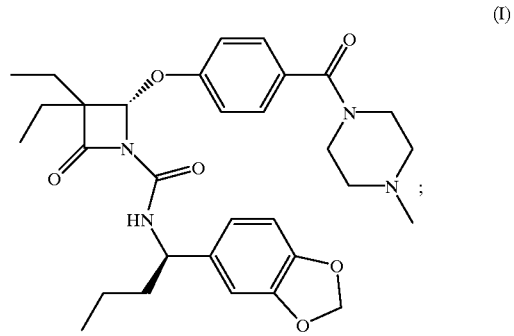

(I)

or a pharmaceutically acceptable salt form thereof.

In a more preferred embodiment, in (e) the strong base is selected from:
  lithium tert-butoxide, potassium tert-butoxide, sodium tert-butoxide, sodium hydride, potassium hydride, tert-butyl lithium, butyl lithium, and sec-butyl magnesium;
the catalytic amount of strong base is about 1 mole percent to about 10 mole percent; and
the coupling solvent is selected from:
  o-xylene, m-xylene, p-xylene, toluene, acetonitrile, ethyl acetate, isopropylacetate, and tert-butyl methyl ether.

In a more preferred embodiment, the compound of formula (VI) is prepared by the process comprising contacting a compound of formula (V):

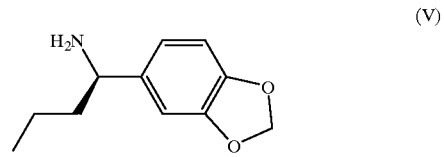

(V)

or a salt form thereof, with phosgene or an equivalent thereof, in a second suitable solvent, at a suitable temperature in the presence of a catalytic amount of a complexing agent.

In an even more preferred embodiment, the second suitable solvent is selected from:
  toluene, o-xylene, m-xylene, p-xylene, and chlorobenzene;
the suitable temperature is about 80° C. to about 135° C.;
the catalytic amount of a completing agent is about 1 mole percent to about 10 mole percent; and
the complexing agent is selected from:
  lutidine, picoline, 1,10 phenanthroline, and pyridine.

In a third embodiment, the present invention describes the formation of a compound of formula (I):

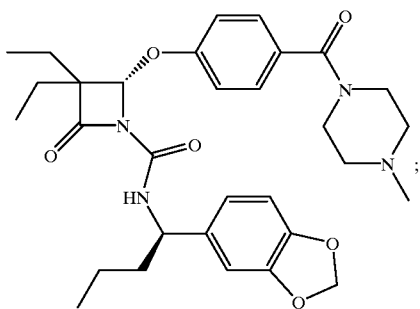

(I)

the process comprising:
(e) contacting a compound of (IV-b):

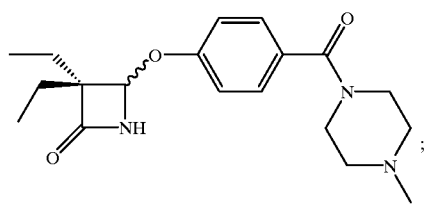

(IV-b)

with a compound of formula (VI):

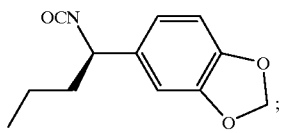

(VI)

in a coupling solvent, in the presence of a catalytic amount of a strong base to form a compound of formula (I), or a pharmaceutically acceptable salt form thereof.

In a preferred embodiment, the strong base is selected from:
lithium tert-butoxide, potassium tert-butoxide, sodium tert-butoxide, sodium hydride, potassium hydride, tert-butyl lithium, butyl lithium, and sec-butyl magnesium;
the catalytic amount of strong base is about 1 mole percent to about 10 mole percent; and
the coupling solvent is selected from:
o-xylene, m-xylene, p-xylene, toluene, acetonitrile, and tert-butyl methyl ether.

In a more preferred embodiment, the strong base is about 3 percent to about 7 percent of potassium tert-butoxide and the coupling solvent is toluene.

DEFINITIONS

The following terms and abbreviations are used herein and defined as follows. The abbreviation: "DAG" as used herein means 2,3:4,6-Di-O-isopropylidene-2-keto-L-gulonic acid monohydrate, "IpAc" as used herein means isopropyl acetate, "THF" as used herein means tetrahydrofuran, "TBME" as used herein means tert-butyl methyl ether, "HPLC" as used herein means high performance liquid chromatograpy, "GC" as used herein means gas chromatography, "ee" as used herein means enantiomeric excess.

The reactions of the synthetic methods claimed herein are carried out in suitable solvents which may be readily selected by one of skill in the art of organic synthesis, said suitable solvents generally being any solvent which is substantially nonreactive with the starting materials (reactants), the intermediates, or products at the temperatures at which the reactions are carried out, i.e., temperatures which may range from the solvent's freezing temperature to the solvent's boiling temperature. A given reaction may be carried out in one solvent or a mixture of more than one solvent. Depending on the particular reaction step, suitable solvents for a particular reaction step may be selected. Such suitable solvents may include, by way of example and without limitation, chlorinated solvents, hydrocarbon solvents, ether solvents, polar protic solvents and polar aprotic solvents.

Suitable halogenated solvents include, but are not limited to carbon tetrachloride, bromodichloromethane, dibromochloromethane, bromoform, chloroform, bromochloromethane, dibromomethane, butyl chloride, dichloromethane, tetrachloroethylene, trichloroethylene, 1,1,1-trichloroethane, 1,1,2-trichloroethane, 1,1-dichloroethane, 2-chloropropane, hexafluorobenzene, 1,2,4-trichlorobenzene, o-dichlorobenzene, chlorobenzene, fluorobenzene, fluorotrichloromethane, chlorotrifluoromethane, bromotrifluoromethane, carbon tetrafluoride, dichlorofluoromethane, chlorodifluoromethane, trifluoromethane, 1,2-dichlorotetrafluorethane and hexafluoroethane.

Suitable hydrocarbon solvents include, but are not limited to benzene, cyclohexane, pentane, hexane, toluene, cycloheptane, methylcyclohexane, heptane, ethylbenzene, m-, o-, or p-xylene, octane, indane, nonane, chlorobenzene, or naphthalene.

Suitable ether solvents include, but are not limited to dimethoxymethane, tetrahydrofuran, 1,3-dioxane, 1,4-dioxane, furan, diethyl ether, ethylene glycol dimethyl ether, ethylene glycol diethyl ether, diethylene glycol dimethyl ether, diethylene glycol diethyl ether, triethylene glycol dimethyl ether, anisole, or t-butyl methyl ether.

Suitable polar protic solvents include, but are not limited to methanol, ethanol, 2-nitroethanol, 2-fluoroethanol, 2,2,2-trifluoroethanol, ethylene glycol, 1-propanol, 2-propanol, 2-methoxyethanol, 1-butanol, 2-butanol, i-butyl alcohol, t-butyl alcohol, 2-ethoxyethanol, diethylene glycol, 1-, 2-, or 3- pentanol, neo-pentyl alcohol, t-pentyl alcohol, diethylene glycol monomethyl ether, diethylene glycol monoethyl ether, cyclohexanol, benzyl alcohol, phenol, and glycerol.

Suitable polar aprotic solvents include, but are not limited to dimethylformamide (DMF), dimethylacetamide (DMAC), 1,3-dimethyl-3,4,5,6-tetrahydro-2(1H)-pyrimidinone (DMPU), 1,3-dimethyl-2-imidazolidinone (DMI), N-methylpyrrolidinone (NMP), formamide, N-methylacetamide, N-methylformamide, acetonitrile, dimethylsulfoxide, propionitrile, ethyl formate, methyl acetate, hexachloroacetone, acetone, ethyl methyl ketone, ethyl acetate, isopropyl acetate, t-butyl acetate, sulfolane, N,N-dimethylpropionamide, nitromethane, nitrobenzene, hexamethylphosphoramide.

As used herein, "aqueous acid" includes, but is not limited to mineral acids such as hydrochloric acid, hydrobromic acid, sulfuric acid, nitric acid, phosphoric acid, lithium bisulfate, potassium bisulfate, sodium bisulfate, and ammonium chloride; and organic acids such as formic acid, acetic acid, trifluoroacetic acid, ethanoic acid, propionic acid, butyric acid, valeric acid and caproic acid.

As used herein, "aqueous base" includes, but is not limited to lithium carbonate, sodium carbonate, potassium carbonate, cesium carbonate, lithium bicarbonate, sodium bicarbonate and potassium bicarbonate.

As used herein, "polar solvent system" refers to a mixture of water and any suitable organic cosolvent or mixture of organic cosolvents mentioned herein, in which the reaction in question produces the desired product.

As used herein, "cosolvent" refers to the solvent which makes up the non-aqueous constituent in a polar solvent system. Cosolvent is intended to include water miscible and water immiscible organic solvents. These solvents may include, by way of example and without limitation, chlorinated solvents, hydrocarbon solvents, ether solvents, polar protic solvents and polar aprotic solvents.

As used herein, "coupling solvent" refers to any solvent in which an amine may be reacted with an isocyanate. Examples of such coupling solvents include, but are not limited to o-xylene, m-xylene, p-xylene, chlorobenzene, toluene, acetonitrile, ethyl acetate, isopropylacetate and tert-butyl methyl ether.

As used herein, "phase transfer catalyst" refers to those agents known in the art of organic synthesis to be capable of facilitating reactions by virtue of their ability to dissolve as ion pairs in both aqueous and organic solvents. Such agents are quaternary ammonium compounds having the structure $R_4N^+X^-$, wherein R=alkyl and X is a counterion (a small, negatively charged species such as chloride, bromide, hydroxide, acetate, sulfate, and the like). Examples of phase transfer agents include, but are not limited to tetrabutylammonium bromide, tetrabutyl-ammonium chloride, tetrabutylammonium iodide, tetramethylammonium hydrogen sulfate, tetramethylammonium bromide, tetramethylammonium chloride, tetramethylammonium iodide, tetrabutylammonium hydrogen sulfate, tetraethyl-ammonium bromide, tetraethylammonium chloride, tetraethyl-ammonium iodide, tetraethylammonium hydrogen sulfate, tetrapropylammonium bromide, tetrapropylammonium chloride, tetrapropyllammonium iodide, tetrapropylammonium hydrogen sulfate, benzyltriethylammonium bromide, benzyltriethylammonium chloride, methyltrioctylammonium bromide, methyl-trioctylammonium chloride, hexadecyltrimethylammonium bromide, hexadecyltrimethylammonium bromide, triethyl-butylammonium bromide, triethylbenzylammonium bromide, trimethylbenzylammonium bromide, triethylbenzylammonium chloride, trimethylbenzylammonium chloride, tripropylbenzylammonium chloride, and the like.

As used herein, "phosgene" refers to the chemical compound with formula $C(=O)Cl_2$; "phosgene equivalent" refers to any agent, capable of reacting with an amine to give an isocyanate, an example includes, but is not limited to triphosgene.

As used herein, "complexing agent" refers to any agent which is capable of preventing racemization of an amine or isocyanate by complexing with iron salts or other metals present as contaminants during a phosgenation reaction, and which lead to epimerization of a chiral center. Examples of such agents include, but are not limited to tertiary aromatic amine bases such as pyridine, pyrimidine, 4-methylpyrimidine, 1,10-phenanthroline, lutidine, and picoline. Lutidine as used herein, refers to 2,3-lutidine, 2,4-lutidine, 2,5-lutidine, 2,6-lutidine, 3,4-lutidine, and 3,5-lutidine. Picoline as used herein, refers to 2-picoline, 3-picoline, and 4-picoline.

As used herein, "strong base" refers to alkoxides, alkyllithiums, metal amides, metal hydrides, metal dialkylamides, and arylamines, wherein; alkoxides include lithium, sodium, and potassium salts of methyl, ethyl, and t-butyl oxides; alkyllithiums include, isobutyllithium, n-hexyllithium, n-octyllithium, n-butyllithium, s-butyllithium, t-butyllithium, phenyllithium, and triphenylmethyllithium; metal amides include sodium amide, potassium amide, and lithium amide; metal hydrides include sodium hydride, potassium hydride, and lithium hydride; and metal dialkylamides include sodium and potassium salts of methyl, ethyl, n-propyl, i-propyl, n-butyl, t-butyl, trimethylsilyl, and cyclohexyl substituted amides.

As used herein, "catalytic amount" refers to an amount which is less than 25 percent of one stoichiometric molar equivalent of starting material.

As used herein, "antisolvent" refers to any solvent which, when added to a polar solvent, results in a decrease of the overall polarity of the solution, typically to effect precipitation of a compound dissolved in the polar solvent. By way of example, and without limitation, such antisolvents include cyclohexane, pentane, hexane, cycloheptane, methylcyclohexane, heptane, tert-butyl methyl ether, and the like.

The compounds described herein may have asymmetric centers. Unless otherwise indicated, all chiral, diastereomeric and racemic forms are included in the present invention. The present invention also includes all isotopes of atoms occurring in the intermediates or final compounds. Isotopes include those atoms having the same atomic number but different mass numbers. By way of general example and without limitation, isotopes of hydrogen include tritium and deuterium; isotopes of carbon include $^{13}C$ and $^{14}C$.

As used herein, "pharmaceutically acceptable salts" refer to derivatives of the disclosed compounds wherein the intermediates or final compound are modified by making acid or base salts of the intermediates or final compounds. Examples of pharmaceutically acceptable salts include, but are not limited to, mineral or organic acid salts of basic residues such as amines; alkali or organic salts of acidic residues such as carboxylic acids; and the like.

The pharmaceutically acceptable salts of the intermediates or final compounds include the conventional non-toxic salts or the quaternary ammonium salts from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts are generally prepared by reacting the free base or acid with stoichiometric amounts or with an excess of the desired salt-forming inorganic or organic acid or base in a suitable solvent or various combinations of solvents.

The pharmaceutically acceptable salts of the acids of the intermediates or final compounds are prepared by combination with an appropriate amount of a base, such as an alkali or alkaline earth metal hydroxide e.g. sodium, potassium, lithium, calcium, or magnesium, or an organic base such as an amine, e.g., dibenzylethylenediamine, trimethylamine, piperidine, pyrrolidine, benzylamine and the like, or a quaternary ammonium hydroxide such as tetramethylammoinum hydroxide and the like.

As discussed above, pharmaceutically acceptable salts of the compounds of the invention can be prepared by reacting the free acid or base forms of these compounds with a stoichiometric amount of the appropriate base or acid, respectively, in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference. The present invention is contemplated to be practiced on at least a multigram scale, kilogram scale, multikilogram scale, or industrial scale. Multigram scale, as used herein, is preferably the scale wherein at least one starting material is present in 10 grams or more, more preferably at least 50 grams or more, even more preferably at least 100 grams or more. Multikilogram scale, as used herein, is intended to mean the scale wherein more than one kilogram of at least one starting material is used. Industrial scale as used herein is intended to mean a scale which is other than a laboratory scale and which is sufficient to supply product sufficient for either clinical tests or distribution to consumers.

The methods of the present invention, by way of example and without limitation, may be further understood by reference to Schemes 1 and 2. Scheme 1 provides the general synthesis for the compound of formula (I). The synthesis of (R)-a-propyl-piperonylamine hydrochloride can be accomplished by methods taught in International Publication WO 97/34887, and the preparation of the β-lactam 3,3-diethyl-4-propionyloxy-2-azetidinone can be accomplished by methods taught in *J. Med. Chem.* 1992, Vol. 35, No. 21, the disclosures of which are hereby incorporated by reference.

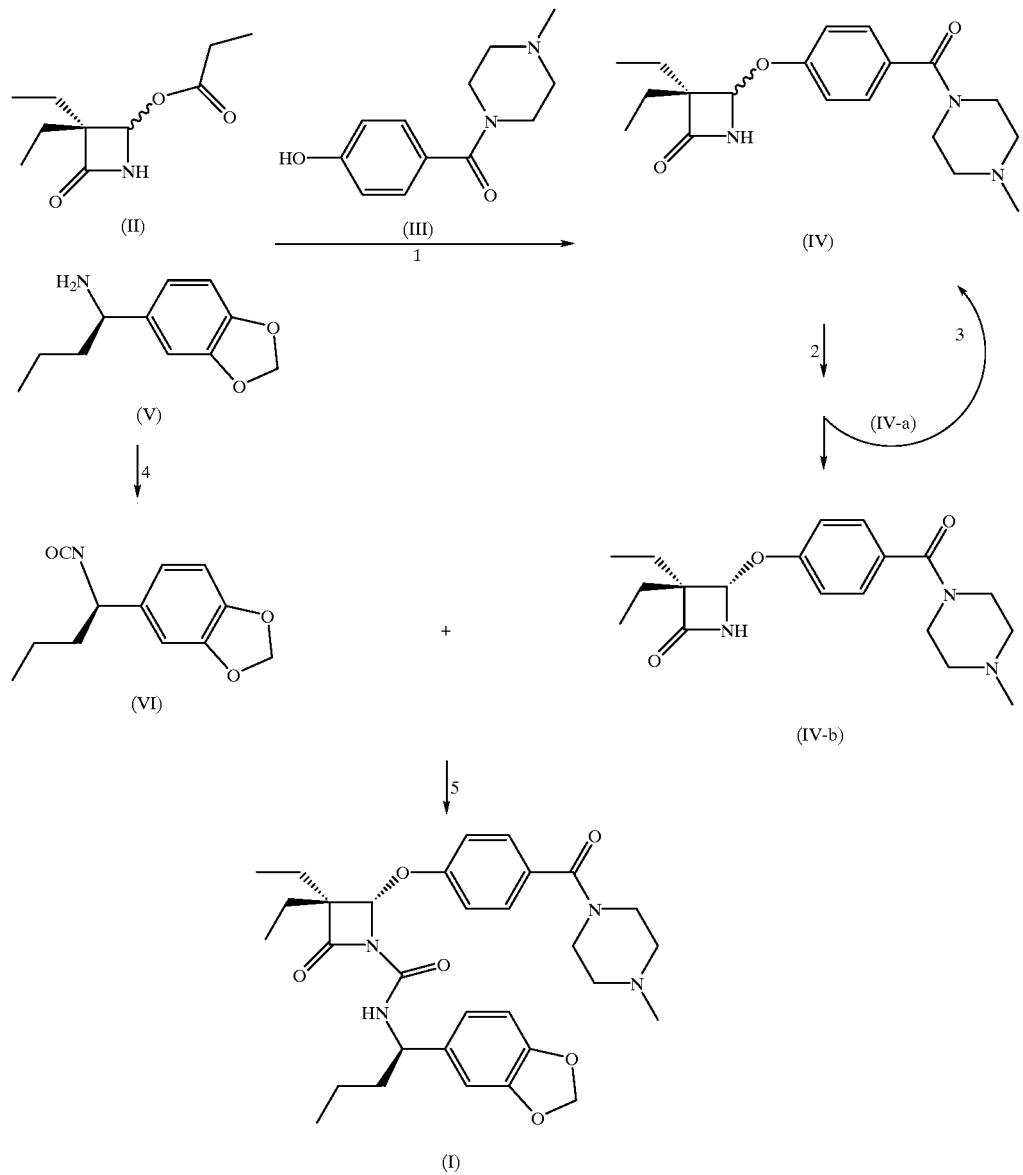

SYNTHESIS

Reaction 1—Condensation

In reaction 1, the propionyloxy ester of 3,3-diethyl-4-propionyloxy-2-azetidinone (II) is displaced with 1-(4-hydroxybenzoyl)-4-methylpiperazine (III) to give the racemic β-lactam (R,S)-1-[4-(3,3-diethyl-4-oxo-2-azetidinyl))oxy]benzoyl]methylpiperazine (IV).

Water is preferably charged to a reaction vessel, followed by about 2 kilograms to about 4 kilograms per liter of an aqueous base. Preferable aqueous bases include lithium carbonate, sodium carbonate, potassium carbonate, and cesium carbonate. Most preferred is potassium carbonate. About 4 percent to about 6 percent of a phase transfer catalyst relative to 3,3-diethyl-4-propionyloxy-2-azetidinone is added. The phase transfer catalyst is typically a quaternized ammonium salt, with tetrabutylammonium hydrogen sulfate, tetrabutylammonium chloride, tetrabutylammonium iodide, or tetrabutyl ammonium bromide being preferred. Tetrabutylammonium hydrogen sulfate is most preferred. The addition may be followed by the charging of 1-(4-hydroxy-benzoyl)-4-methylpiperazine (III), preferably in an amount of about 0.9 molar equivalents to about 1.0 molar equivalents relative to 3,3-diethyl-4-propionyloxy-2-azetidinone (II). More preferred is about 0.95 to about 0.99 molar equivalents. A cosolvent is then charged to create a polar solvent system. Preferred cosolvents include those which will result in a biphasic mixture under the reaction conditions disclosed herein. Preferred cosolvents include, but are not limited to, isopropyl acetate, methyl acetate, ethyl acetate, tert-butyl acetate, toluene and tert-butyl methyl ether. Isopropyl acetate is most preferred. Under preferred conditions, the reaction mass is a three phase system of liquid aqueous and organic phases, with the piperazine amide (III) as suspended solids. After warming to about 30° C. to about 60° C., a solution of about 70 percent to about 90 percent w/w content of 3,3-diethyl-4-propionyloxy-2-azetidinone (II), preferably dissolved in the cosolvent, is added over about 1 hour to about 2 hours. The piperazine amide (III) likely dissolves as the reaction proceeds, resulting in both aqueous and organic liquid phases. After holding the reaction temperature at about 40° C. to about 50° C. for about one hour, reaction progress may be monitored by HPLC. Typically, <0.5 percent piperazine amide is present at a reaction time of 1 hour. Preferably, there is <0.5 percent of total area remaining for piperazine amide at reaction completion. More preferred is <0.2 percent area for the piperazine amide. The reaction may be stirred until this completion criterion is met, afterwhich the lower, aqueous layer may be separated and the upper, organic phase concentrated, preferably under reduced pressure. An antisolvent, which includes those known in the art of process chemistry to be suitable for precipitating a product dissolved in a more polar solvent, is charged. Preferably, the antisolvent is a hydrocarbon such as pentane, hexane, heptane, or mixtures thereof. Heptane is most preferred. Following the addition of the antisolvent, the mixture is preferably stirred for a suitable period of time, at a temperature appropriate for crystallization. By way of general example, about 8 to about 12 hours at about 10° C. to about 20° C., followed by about 1 to about 4 hours at about −20° C. to about 0° C. is sufficent for adequate crystallization. The crystals are recovered, preferably by filtration. The wet cake may be returned to the vessel, if desired, and slurried with additional antisolvent to assure product consistency and maximum product recovery from the vessel. The crystalline 1-[4-(3,3-diethyl-4-oxo-2-azetidinyl))oxy]benzoyl]methylpiperazine (IV) is preferably dried in an oven at about 40° C. to about 60° C., at a vacuum of about 40 mm to about 60 mm to a constant weight.

Reaction 2—Resolution

In reaction 2, the racemic β-lactam (R,S)-1-[4-(3,3-diethyl-4-oxo-2-azetidinyl))oxy]benzoyl]methylpiperazine (IV) is resolved into its solid (R) DAG salt (IV-a) by reaction with 2,3:4,6-Di-O-isopropylidene-2-keto-L-gulonic acid (DAG). The desired (S)-isomer (IV-b) may be isolated from the mother liquor.

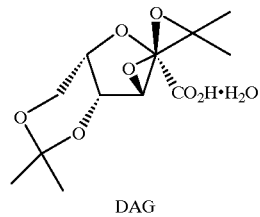

DAG

Into a first vessel, 2,3:4,6-Di-O-diisopropylidene-2-keto-L-gulonic acid (DAG), preferably as the monohydrate in an amount which is preferably about 50 mole percent relative to the racemic β-lactam (IV), is slurried in about 3 mL to about 6 mL per gram of a suitable solvent (relative to the subsequent racemic β-lactam charge), and heated with stirring to about 30° C. to about 80° C. More preferred is heating to about 60° C. to about 80° C. While numerous solvents are possible, preferred suitable solvents include polar solvents such as isopropyl acetate, methyl acetate, ethyl acetate, tert-butyl acetate, and acetone. Most preferred is isopropyl acetate. The solution is typically very pale yellow and slightly hazy.

A second vessel is preferably charged with the polar solvent chosen above in an amount which is about 6 mL to about 10 mL per gram relative to the racemic β-lactam (IV), and is followed by a small DAG charge. The purpose of the DAG charge is to minimize chemical degradation of the racemic β-lactam during heating. The amount of DAG is preferably about 1 mole percent to about 15 mole percent relative to the racemic β-lactam. More preferred is about 8 percent to about 12 percent. The racemic β-lactam is preferably charged to the vessel, and the resulting slurry heated to an elevated temperature sufficient to give a clear solution. Preferred temperatures are about 60° C. to the reflux temperature of the solvent. Most preferred is the use of isopropyl acetate and heating to about 65° C. to about 75° C. The solution of DAG in the first vessel may then be added at a constant rate to the racemic β-lactam (IV) solution over about 1 to about 5 hours. More preferred is adding the solution over about 2 hours to about 3 hours. The suspension is preferably allowed to cool to about 15° C. to about 25° C. over about 1 hour to about 5 hours and held with stirring for an additional period of time sufficient to reach the maximum enantiomeric excess. A stir time of several hours, preferably greater than about 5, is preferred.

By way of example, an in-process control may be employed to monitor reaction progression. Following about 6 hours of stirring at about 20° C., a reaction sample is removed from the vessel and filtered with vacuum. The (R) β-lactam.DAG cake (VI-a) is thoroughly washed with solvent (approximately equal to the filtrate volume). The cake and filtrate are analyzed by HPLC for chemical and chiral purity. The HPLC trace will indicate the reaction profile, specifically, the extent of chemical degradation of the racemic β-lactam (IV). The filtrate and washes are typically very close in value (no more than 2–3% difference) for the enantiomeric excess of the (S) β-lactam (IV-a) contained. In order to proceed, the enantiomeric excess (e.e.) in the reaction liquors is preferably at least .90 percent. If the e.e. is lower, an additional 5 mole percent of DAG may be added and the suspension stirred at ambient temperature for at least an additional 2 hours before further sampling. A second additional charge of DAG is generally not necessary, but may be performed if the e.e. is substandard.

Once the enatiomeric excess has reached an acceptable level, the mother liquor is separated from the (R) β-lactam.DAG cake (IV-b), preferably by filtration. For large scale reactions, the cake may be isolated by centifuging the mixture and washing the wet cake with a the reaction solvent, followed by spinning. The mother liquors are preferably transferred back to the reaction vessel, which may be cleaned with a water wash and methanol boil-out prior to recharging. The liquors are preferably washed with an aqueous base solution having a concentration of about 5 percent to about 20 percent by weight. The preferred aqueous bases are potassium bicarbonate, lithium bicarbonate, and sodium bicarbonate. Potassium bicarbonate is most preferred. The layers are preferably separated and the organics washed with an aqueous salt solution. Aqueous sodium chloride is preferred. Separation of these layers may be slow. The organic solution may be concentrated by distillation under reduced pressure. After approximately half of the reaction solvent has been removed, an antisolvent is preferably charged to the vessel. Preferred antisolvents include pentane, hexanes, heptane, tert-butyl methyl ether, or mixtures thereof. Most preferred is heptane. The removal of solvent may be resumed until a desired solvent composition is achieved, preferably as measured by gas chromatography. Suitable conditions for the measurement of solvent ratios by gas chromatography will be readily understood by one skilled in the art. Preferably, the composition is about 25 percent to about 40 percent polar solvent to about 60 percent to about 75 percent antisolvent. The mixture may then be cooled slightly below room temperature and stirred before any additional antisolvent is charged to achieve the desired composition. Chiral analysis of a reaction sample by HPLC preferably shows the liquors to be about 60 percent to 100 percent e.e. for (S) β-lactam (IV-a). More preferred is about 70 percent to about 100 percent. Most preferred is about 80 percent to about 100 percent. The precipitated (S) β-lactam is isolated, preferably by filtration. The wet cake may be washed with a hydrocarbon solvent such as pentane, hexane or heptane with the most preferred being heptane. The cake is preferably dried to a constant weight, afterwhich weight percent, impurity profile, water content, and enantiomeric integrity may be determined.

Reaction 3—Racemization

In reaction three, the (R)-1-[4-(3,3-diethyl-4-oxo-2-azetidinyl))oxy]benzoyl]methylpiperazine DAG salt (IV-a) is free based and racemized to give the compound of formula (IV). This procedure is preferably performed more than once to optimize recovery.

Free-basing (IV-a)

The process of the present invention includes the recycling of the (R)-β-lactam isomer from reaction 2 by liberation from DAG with aqueous base. Water is preferably charged to a vessel, followed by an aqueous base such as lithium carbonate, sodium carbonate, potassium carbonate or cesium carbonate. Most preferred is potassium carbonate. The amount of base is preferably about 3 equivalents to about 5 equivalents of about a 30 percent to 40 percent aqueous solution. Aqueous sodium chloride may also be added to better define the layers. The mixture is preferably stirred until the solids dissolve. The (R)-β-lactam.DAG salt is charged, preferably followed by a cosolvent which typically results in a biphasic mixture. Preferred cosolvents include isopropyl acetate, ethyl acetate, methyl acetate, and tert-butyl acetate. Most preferred is isopropyl acetate. The aqueous layer is preferably withdrawn and charged to another vessel after about 10 minutes to about 20 minutes. This solution is then extracted with fresh cosolvent and combined with the original organic solution.

Recovery of 2,3:4,6-Di-O-isopropylidene-2-keto-L-gulonic acid monohydrate (DAG)

The resultant aqueous layers from the free-basing step may be combined and treated with aqueous acid to precipitate the DAG monohydrate. Preferred acids include, but are not limited to hydrochloric acid, sulfuric acid, and nitric acid. Most preferred is hydrochloric acid. The DAG monohydrate is preferably isolated by filtration, dried under vacuum and reused for resolutions of the racemic β-lactam.

Racemization of (IV-a)

To the free base solution isolated above is added piperazine amide in an amount of about 8 mole percent to about 12 mole percent. The purpose of the amide is to retard the decomposition of the racemic β-lactam. A phase transfer catalyst is preferably added to the reaction vessel. Preferred phase transfer agents include quaternary ammonium salts such as tetrabutylammonium hydrogen sulfate tetrabutylammonium chloride, tetrabutylammonium iodide, and tetrabutylammonium bromide. Tetrabutyl ammonium bromide is preferred. To the mixture, an solution of aqueous base preferably having a concentration of about 40 percent to about 70 percent is charged. Preferred aqueous bases include sodium carbonate, lithium carbonate, potassium carbonate and cesium carbonate. Most preferred is potassium carbonate. The mixture may be heated at about 50° C. to about 60° C. for about 2 to about 3 hours. Most preferably, the reaction is heated until the e.e. of the mixture is less than about 2 percent, or until the impurity levels begin to rise beyond what is desired. By way of example, if the total area percent response for racemic β-lactam reaches 90 percent or less, then racemization should be stopped to avoid material loss due to poor crystallization efficiency. The mixture is preferably cooled to about 20° C. to about 25° C., and the phases separated. The organic layer may be extracted with the aqueous base solution used in the racemization, and may also be washed with an salt solution such as aqueous sodium chloride. The organic layer is preferably concentrated under reduced pressure to remove about 65 percent to about 75 percent of the original volume. To this solution at about 30° C. to about 40° C. is added an antisolvent. Preferred antisolvents include diethyl ether, tert-butyl methyl ether, heptane, hexane, pentane, and mixtures thereof. Most preferred is tert-butyl methyl ether. The solution may be cooled following the addition of the antisolvent and held for about 2 hours or more. Most preferably, the crystallization is considered complete when the solution contains.2.75 percent w/w content of racemic β-lactam. The racemic β-lactam may be isolated by centrifuge with recycling of the mother liquors, and continuous washing of the cake with additional antisolvent. The racemic β-lactam is preferably dried in an oven at about 40° C. to about 60° C., at a vacuum of about 40 mm to about 60 mm to a constant weight.

Reaction 4—Isocyanate Formation

In reaction 4, (R)-a-propyl-piperonylamine (V) or a salt form thereof is reacted with phosgene or a phosgene equivalent in the presence of a complexing agent to form (R)-5-(1-isocyanatobutyl)-1-3-benzodioxole (VI).

Upon scale-up, it was observed that the enantiomeric excess of (R)-a-propyl-piperonyl amine falls to zero during phosgenation. Experiments designed to probe this problem confirmed that ppm levels of iron, most likely present as dissolved ferric chloride, racemized the starting material during the course of the reaction. Based on rigorous experimentation, it was discovered that the epimerization could be prevented by the addition of about 3 mole percent to about 7 percent mole percent of an agent capable of complexing with the dissolved iron species. More preferred is the addition of about 3 mole percent to about 6 mole percent of a complexing agent. Preferred complexing agents include aromatic amines such as 1,10 phenanthroline, pyridine, pyrimidine, lutidine, and picoline. More preferred are pyridine, picoline, and 1,10 phenanthroline. Most preferred is pyridine. The use of these complexing agents also reduces at least one known side reaction that gives a 3,4-methylenedioxy-1-butene benzene impurity which has been identified by mass spectra and NMR.

Thus, into about 7 mL per gram to about 15 mL per gram of a suitable solvent is preferably charged (R)-a-propyl piperonyl-amine.HCl (V-i) and a complexing agent. Suitable solvents include, but are not limited to toluene, o-xylene, m-xylene, p-xylene and chlorobenzene. Phosgene or a phosgene equivalent such as triphosgene is preferably charged to the vessel below the surface of the toluene, directly from the gas phase of a cylinder. The preferred amount of phosgene (or equivalent) is about 1.0 molar equivalents to about 1.5 molar equivalents. More preferred is about 1.2 molar equivalents to about 1.4 molar equivalents. The solution temperature may be kept from about 0° C. to about 110° C. during the addition. More preferred is about 90° C. to about 110° C. Once the phosgene reagent is introduced, the reacton may be kept at a temperature of about 0° C. to about 110° C., but is preferably held at reflux for about 15 minutes to about 45 minutes followed by cooling to about 80° C. to about 100° C. The reaction may be sparged at this temperature with nitrogen to purge remaining gaseous reagent. The isocyanate formation may also be monitored by HPLC to judge reaction progress. The reaction mass, if heated is preferably cooled to about 0° C. to about 10° C. and quenched into about a 5 percent to about 20 percent aqueous sodium or potassium bicarbonate solution, while maintaining the temperature between about 0° C. to about 10° C. The most preferred bicarbonate for the quench is potassium bicarbonate. The solution may then be washed with water while maintaing the constant reduced temperature. The organic solution is preferably dried after isolation. While numerous drying methods are possible including the use of drying agents, azeotropic vacuum distillation at about 40° C. to about 50° C. and a vacuum of about 40 mm to about 50 mm is preferred. The dry solution of (R)-isocyanate (VI) may be used directly in the next reaction, or stored, provided reasonable efforts are made to avoid contact with moisture, which will be readily understood by one skilled in the art.

Reaction 5—Coupling

In reaction 5, (R)-5-(1-isocyanatobutyl)-1-3-benzodioxole (VI) is reacted with (S)-1-[4-(3,3-diethyl-4-oxo-2-azetidinyl))oxy]benzoyl]methylpiperazine (IV-b) to give [S-(R,S)]-N-[1,3-benzodioxol-5-yl)butyl]-3,3-diethyl-2[4-[4-methyl-1-piperazinyl)carbonyl]phenoxy]-4-oxo-1-azetidine carboxamide (I).

Preferably, a coupling solvent is charged to the reaction vessel and stirred at about −25° C. to about 25° C. More preferred is about −5° C. to about 5° C. Suitable coupling solvents include o-xylene, m-xylene, p-xylene (or mixtures thereof), toluene, acetonitrile and tert-butyl methyl ether. Most preferred is toluene. The β-lactam (S)-1-[4-(3,3-diethyl-4-oxo-2-azetidinyl))oxy]benzoyl]methylpiperazine (IV-b) is preferably charged followed by a Karl-Fischer (KF) determination of the supernatant solution. The preferred amount of β-lactam (IV-b) is about 0.90 equivalents to about 0.98 equivalents based on the (R)-isocyanate. More preferred is about 0.94 equivalents to about 0.96 equivalents. The water content is preferably reduced if the level is above 350 ppm. This may be accomplished by the addition of excess coupling solvent and subsequent distillation. Once the desired solution composition is obtained, a second solution containing about 1 molar equivalent of the (R)-isocyanate (VI) in the coupling solvent is preferably charged to the vessel. The composition of the solution is preferably about 15 percent to about 20 percent w/w solution. The reaction slurry may be cooled to about −78° C. to about 20° C. prior to further addition. More preferred is to cool the solution to about −20° C. to about 0° C. A catalytic amount of a strong base is preferably added after cooling. Preferred strong bases include sodium hydride, butyl lithium, tert-butyl lithium, sec-butyl magnesium, and alkyl metal oxides such as lithium, sodium and potassium salts of methyl, ethyl and t-butyl oxides. More preferred is lithium tert-butoxide, sodium tert-butoxide, and potassium tert-butoxide. Most preferred is lithium tert-butoxide. The strong base may be added as a solution in a concentration of about 1M solution of base in a hydrocarbon or other suitable solvents known to one skilled in the art as commercially available. The strong base is preferably present in an amount of about 1 mole percent to about 10 mole percent relative to the (S) β-lactam (IV-b). More preferred is about 3 mole percent to about 10 mole percent. Most preferred is about 4 percent to about 6 percent. A modest exotherm may accompany the addition, and as such, the solution may be cooled prior to charging. Typically the (S) β-lactam (IV-b) dissolves within about 15 to about 60 minutes to give a light yellow solution. HPLC analysis may be performed to judge reaction completion. The reaction is considered complete preferably when HPLC result show about <0.1 percent total area response for the (R)-isocyanate (VI) and about 0.1 to about 1.2 percent unreacted (S) β-lactam (IV-b). When the reaction is considered complete, it may be quenched with an appropriate acid. It will be readily understood in the art that numerous acids such as hydrochloric acid, nitric acid, sulfuric acid, ammonium chloride, sodium bisulfate, and organic acids are acceptable for quenching purposes, glacial acetic acid is preferred. The reaction solution may be washed with an aqueous salt solution, such as about 2 percent aqueous sodium chloride. After separation of the aqueous layer, the reaction is preferably concentrated to below about one-half the original volume by vacuum distillation. By way of example, the solution may be distilled at about 40° C. under a pressure of about 60 mm. The warm reaction solution may be filtered for clarification purposes. One or more antisolvents may be added to precipitate the product. Suitable antisolvents include tert-butyl methyl ether, diethyl ether, hexane, heptane, pentane or mixtures thereof. Most preferred is the addition of tert-butyl methyl ether and heptanes over about 1 hour (depending on scale) while keeping the temperature at about 25° C. to about 60° C. The product preferably precipitates during the antisolvent addition. The solution may be held at the elevated temperature for an additional time to assure maximum crystallization, then cooled at a constant rate to about −20° C. to about −5° C. over 5 or more hours. The product is preferably isolated by filtration or by general centrifuge procedures known to one skilled in the art, and the cakes washed with a second antisolvent. Preferred second antisolvents include tert-butyl methyl ether, diethyl ether, hexane, heptane, and pentane or mixtures of these solvents in toluene. Most preferred is a mixture of hexanes and toluene in a ratio of about 1 percent to about 99 percent hexanes, precooled about −20° C. The wet cake may be dried to a constant weight in a vacuum tray oven at about 30° C. about 50° C. under reduced pressure. The preferred pressure is about 45 mm to about 55 mm. The purity and chiral integrity of compound (I) may be ascertained by HPLC analysis, using conditions disclosed herein.

The methods of the present invention, may be further understood by reference to Scheme 2, which provides an example of specific conditions suitable for the formation of the compound of formula (I).

Other features of the invention will become apparent in the course of the following descriptions of exemplary embodiments which are given for illustration of the invention, and are not intended to be limiting thereof.

EXAMPLE 1

(R,S)-1-[4-[(3,3-diethyl-4-oxo-2-azetidinyl)oxyl]]benzoyl]methylpiperazine (IV)

Water (219 L) was charged to the vessel, followed by 137 kg, (993 mol) of potassium carbonate. This charge was

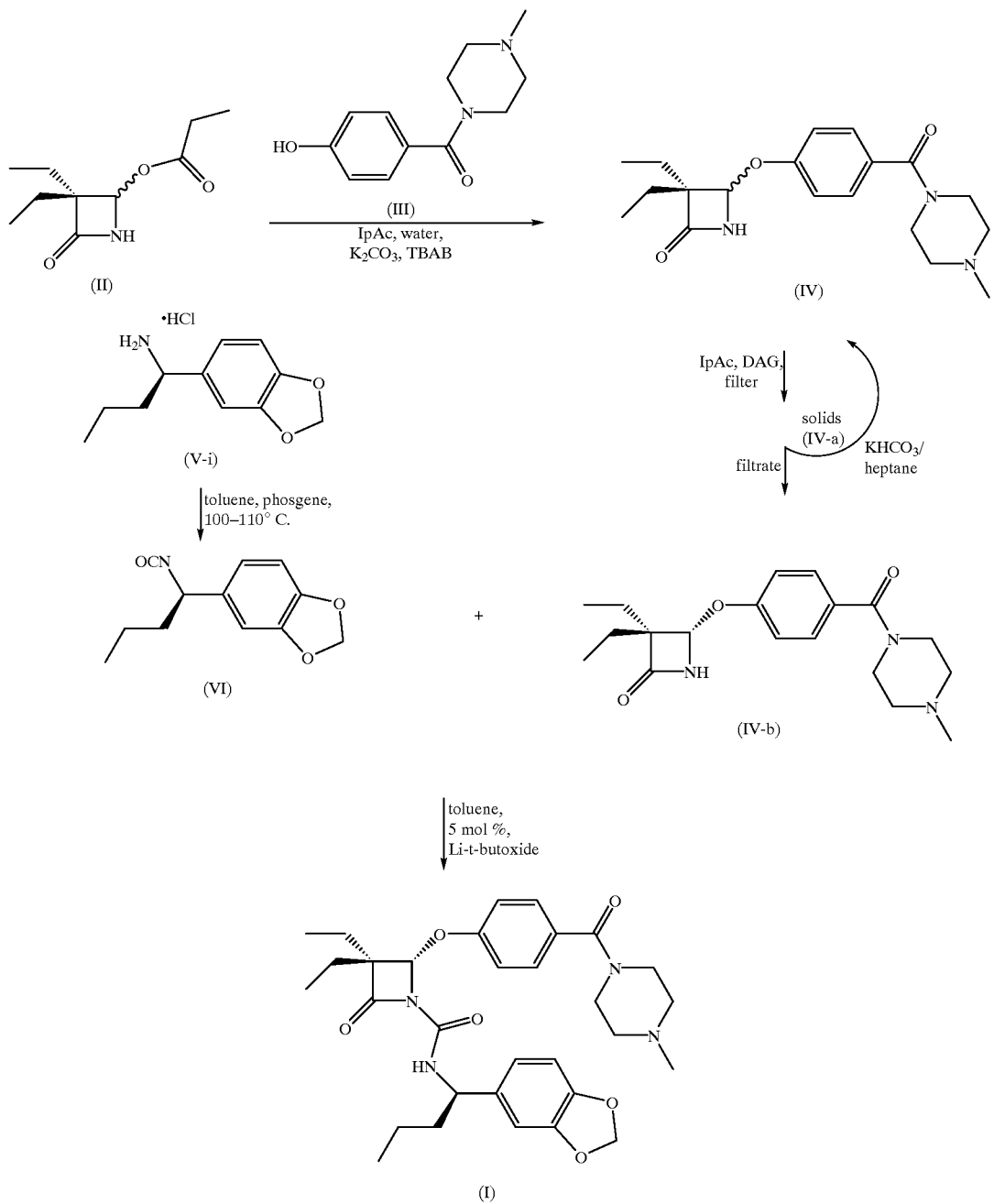

Scheme 2 followed by the addition of 415 g (1.2 mol, about 4.8 mol % vs. 3,3-diethyl-4-propionyloxy-2-azetidinone) of tetra-butylammonium hydrogen sulfate and 56 kg (244 mol, 0.97 mol eq. relative to 3,3-diethyl-4-propionyloxy-2-azetidinone) of piperazine amide (III). After charging in 330 L of isopropyl acetate, the reaction mass is a three phase system of liquid aqueous and organic phases, with suspended solids (piperazine amide (III)). After warming to 45° C., a solution of 59 kg (85% w/w content, 251 mol) of 3,3-diethyl-4-propionyl-oxy-2-azetidinone (II) in 56 L of isopropyl acetate was added over 1.2 hours. The piperazine amide dissolved as the reaction proceeds, resulting in aqueous and organic liquid phases. After holding at 45° C. for one hour, the reaction was observed to be complete by HPLC (<0.2% of total area remaining for piperazine amide versus the completion criterion of less than 5% piperazine amide). The lower, aqueous layer was separated and the upper, organic phase was concentrated under reduced pressure (100 mm/40° C.) to about 250 L. tert-Butyl methyl ether (250 L) was added and the mixture was stirred for 10 h at 15° C. while the product slowly crystallized (this stirring time is carried out for convenience only, the reaction was typically held overnight at this point). After cooling to −10° C. over 2 hours the product was filtered on a pressure Nutsche filter and the wet cake was returned to the vessel and slurried with 290 L of tert-butyl methyl ether. The slurry was cooled to −5° C. and filtered on a pressure Nutsche filter to isolate (2% yield loss seen in the filtrate) the (R,S)-1-[4-[(3,3-diethyl-4-oxo-2-azetidinyl)oxy]]benzoyl]methylpiperazine (β-lactam) cake. After drying at 50° C. and 50 mm in a vacuum oven to a constant weight, 75.6 kg of (R,S) β-lactam (IV) was obtained as a white solid with 98.0% w/w purity, and 88% yield, corrected for the purity of both starting material and product. A second batch was run as described above, but utilizing 224 moles of piperazine amide. The reaction yielded an isolated product weight of 67 kg, having 100% w/w purity, and an 86% corrected yield. The reslurry volume of tert-butyl methyl ether was increased to 550 L in the second run.

HPLC Assay Method

Column: Zorbax SB-phenyl 15 cm×4.6 mm id.
Mobile Phase:
Buffer: 0.1% v/v trifluoroacetic acid in water
Organic: 0.1% v/v trifluoroacetic acid in acetonitrile
Flow Rate: 1.0 ml/minute
Oven Temperature: ambient (20° C.)
Detection: UV, 240 nm wavelength
Injection Volume: 5 μml
Run Time: 35 minutes
Gradient (linear):

| Time | % Buffer | % Acetonitrile |
| --- | --- | --- |
| 0 | 95 | 5 |
| 5 | 95 | 5 |
| 15 | 50 | 50 |
| 20 | 50 | 50 |
| 25 | 10 | 90 |
| 30 | 0 | 100 |

Retention Times

| piperazine amide (III) | 5.2 minutes |
| --- | --- |
| Racemic β-lactam (IV) | 14.2 minutes |

EXAMPLE 2

Resolution of (R,S)-1-[4-[(3,3-diethyl-4-oxo-2-azetidinyl) oxyl]benzoyl]methylpiperazine (IV) to (S)-1-[4-[(3,3-diethyl-4-oxo-2-azetidinyl)oxy]] benzoyl]methylpiperazine (IV-b)

2,3:4,6-Di-O-diisopropylidene-2-keto-L-gulonic acid (DAG, 28.3 kg, 96.6 moles, 50 mol % relative to the racemic β-lactam) was slurried in 266 L of isopropyl acetate (4 mL/g relative to the subsequent racemic β-lactam charge) and heated with stirring to 70° C. in a 200 gallon, glass-lined vessel. This gave a very pale yellow, slightly hazy solution. A 300 gallon, glass-lined vessel was charged with 532 L of isopropyl acetate (8 ml/g relative to racemic β-lactam (IV) followed by a small DAG charge (5.7 kg, 19.3 moles, 10 mol %). Racemic β-lactam (IV) (66.8 kg, 193 moles) was then charged and the resulting slurry was heated to 70° C. to give a clear solution. The solution of DAG in isopropyl acetate from the 200 gallon vessel was then added at a constant rate to the racemic lactam solution over 2.5 hours. The suspension was cooled to 20° C. over 3 hours and held with stirring for an additional 11.5 hours.

Chiral HPLC indicated that the (R) β-lactam.DAG cake (IV-a) was about 92% e.e. after washing with isopropyl acetate, and the liquors were approximately 93% e.e. for (S) β-lactam (IV-b). The crude cake had an e.e. of about 70% for the (R) β-lactam.DAG cake (IV-a), while the cake wash liquors had about 92% e.e. for the (S) β-lactam (IV-b). Based on these results, the mother liquors were directly combined with the resolution liquors and processed together. The (R) β-lactam.DAG cake (IV-a) was filtered in seven drops to the centifuge and each wet cake was washed with 25 kg of isopropyl acetate with spinning. This material was later dried to give a constant weight of 62.9 kg of (IV-a). The e.e.'s of these various wet cakes are as follows:

| cake | wet weight (IV-a) | e.e. |
| --- | --- | --- |
| 1 | 19.3 kg | 92.5% |
| 2 | 20.8 kg | 92.9% |
| 3 | 19.8 kg | 93.6% |
| 4 | 18.8 kg | 92.8% |
| 5 | 19.0 kg | 92.2% |
| 6 | 21.8 kg | 91.8% |
| 7 | 16.7 kg | 92.2% |

The e.e. of the final combined mother liquors and wash was 93.2% for the (S) β-lactam (IV-b). The liquors were transferred back to the (cleaned with a water wash and methanol boil-out) 300 gallon vessel and washed with 20% aqueous, potassium bicarbonate solution. The layers were separated and the organic was washed with 188 kg of 15% aqueous, sodium chloride solution. Separation of these layers was slow. The isopropyl acetate solution was concentrated by distillation at about 100 mm Hg/40° C. A total of 440 kg (460 L) of isopropyl acetate was collected out of a total of approximately 1000 L. Vacuum was released and 235 kg of heptanes (340 L) was charged to the vessel. Vacuum, heating and distillation were resumed (480 kg collected) until a final volume of approximately 110 L was reached. GC analysis showed the composition of the solvent to be about 60–40% isopropyl acetate in n-heptane with the target being 25–40% isopropyl acetate. After cooling to 20° C. and stirring for 9 h, an additional 60 kg of heptanes was added and the mixture was stirred at 20° C. for 2 h. Analysis of a reaction sample showed the liquors to be about 78.9% e.e. for (S) β-lactam (IV-b). A w/w assay showed the liquors contained only about 350 g of (IV-b) by w/w assay (concentration of 0.19% w/w for racemic β-lactam (IV) in 207 kg of liquors with an e.e. of 78.9%). The precipitated (S) β-lactam (IV-b) was filtered. The wet cake had an e.e. of 93.9% and was washed with 100 kg of heptanes. The wet cake had a crude weight of 34.7 kg. After drying to a constant weight, 31.0 kg of material was obtained. The dried product had a w/w assay of 101.9% with an impurity profile of 100%. A Karl Fischer determination showed 0.29% water by weight and the e.e. was 94.1%. The yield corrected for assay of both starting material and product was 91.6%.

HPLC Chiral Assay Method

Column: Chiracel OD 4.6 mm×25 cm, 10 um
Detector: UV, 240 nm wavelength
Mobile Phases:
A: hexane
B: ethanol
C: 2-propanol
Oven Temp.: 40° C.
Injector Vol.: 5 ml
Flow Rate: 1.0 mL/minute
Gradient:
90:10:0 ratio of A:B:C at t=0;
linear gradient to 80:20:0 at 10 minutes
linear gradient to 75:20:5 at 15 minutes
linear gradient to 65:20:15 at 20 minutes
linear gradient to 60:20:20 at 25 minutes
Retention Times:
(S) β-lactam (IV-b): 13.0 minutes
(R) β-lactam (IV-a): 18.4 minutes

EXAMPLE 3

Racemization of (R)-1-[4-[(3,3-diethyl-4-oxo-2-azetidinyl) oxy]]benzoyl]methylpiperazine DAG salt (IV-a) to (R,S)-1-[4-[(3,3-diethyl-4-oxo-2-azetidinyl)oxy]]benzoyl]methyl piperazine (IV)

Water (288 L) was charged to a 300-gallon vessel, followed by 52.5 kg of potassium carbonate (4 eqs, 35% aqueous solution) and 34.5 kg of sodium chloride. The mixture was stirred for 15 minutes by which time the solids had dissolved. (R) β-lactam.DAG (IV-a) (72.5 kg, 117 mol) was added over 5 minutes. Isopropyl acetate (442 kg) was charged to this solution using deadhead vacuum. The biphasic mixture was agitated for 15 minutes and the aqueous layer was withdrawn and charged to a 200 gallon reactor. This solution was extracted with 316 kg of isopropyl acetate and the extract combined with the original organic solution in the 300 gallon reactor. To this solution was added 2.6 kg of piperazine amide (III) (10 mol %, added to retard the decomposition of racemic β-lactam (IV), 188.6 g of tetrabutylammonium bromide, and a preformed solution of aqueous potassium carbonate (103 L water, 64.7 kg of solid potassium carbonate). The mixture was then heated at 60° C. (typically 2–3 h) until the e.e. of the mixture was less than 2% or the impurity levels began to rise (if the total area % response for racemic β-lactam (IV) reaches 90% or less then racemization should be stopped to avoid material loss due to poor crystallization efficiency). The mixture was then cooled to 20–25° C. and the phases separated. The isopropyl acetate layer was extracted with 60 L of 25% aqueous potassium carbonate solution and washed with 75 kg of 20% aqueous sodium chloride solution. The isopropyl acetate layer was concentrated at 40–50° C./40–50 mm vacuum to remove about 790 L of solvent (about ⅓ to ¼ of original volume remained). To this solution at 30° C. was added 86.6 kg of tert-butyl methyl ether. The solution was cooled to 20° C. over 1 h and held for at this temperature for 2 h. The suspension was then cooled to −10° C. over 1 h and held at this temperature for 2 h. The crystallization was complete when the solution contained.2.75% w/w content of racemic β-lactam (IV). The product was isolated by centrifugation with recycling of the mother liquors, and the cake washed with 15 kg of tert-butyl methyl ether. The racemic β-lactam (IV) was dried at 40° C. and about 50 mm pressure until a constant weight was reached and gave 34 kg (86% yield) with 3.66% e.e. by HPLC method reported in Example 2.

EXAMPLE 4

(R)-5-(1-isocyanatobutyl)-1,3-benzodioxole (VI)

Into 77 L of toluene was charged 7.7 kg of R-amine HCl (V-i) (99.2% ee) and 5 mole % pyridine as a complexing agent to inhibit racemization. The phosgene (4.0 kg, 1.35 moles) was added as a gas below the surface of the toluene, directly from the gas phase of the phosgene cylinder. The solution temperature was kept at 100–110° C. during this addition. After all the phosgene was introduced, the reacton mass was held at reflux (typically 106–109° C.) for an additional 30 minutes and then cooled to 90° C. The reaction was sparged at this temperature by the introduction of nitrogen below the surface of the liquid. The reaction was >98% complete, by HPLC, at this point. The reaction mass was cooled to 0–10° C. and then quenched into 5% aqueous sodium bicarbonate which was cooled to 0–10° C. The solution was kept at this temperature during the quench. The quench was followed by two water washes of 35 L, all at 5–10° C. The azeotropic distillation to remove water from the toluene solution of the isocyanate was carried out at a pot temperature of 40–50° C. and a vacuum of 40–50 mm. This gave 38.8 kg of a 17.33 wt % solution in toluene of the (R)-isocyanate (VI), 94% yield and 99.6%ee.

HPLC Assay Method

Column: Zorbax SB -Phenyl, 4.6 mm×15 cm, 5 μm.
Mobile Phases:
Buffer solution: 0.05 M aqueous Ammonium Acetate (3.854 g in 1 liter water);
Methanol; and
Acetonitrile
Gradient:
Linear gradient applied over 25 minutes by varying the amounts of aqueous buffer and acetonitrile, while holding the amount of methanol constant, as given below:
A: 50% Buffer–25 min→20% Buffer
B: 20% MeOH–25 min→20% MeOH
C: 30% CH$_3$CN–25 min→60% CH$_3$CN
Flow rate: 1.0 mL/min
Oven temp.: 40° C.
Detector: UV, 235 nm wavelength
Injector vol.: 5 μL
Stop time: 25 minutes
Retention Times:
(R)-amine HCl (V-i): 3.6 minutes
(R)-isocyanate (VI): 10.1 minutes HPLC Chiral Assay Method Column: Chiralpak AD, 4.6 mm×25 cm, 10u
Mobile Phase: Hexane:methanol 98:2
Flow rate: 1.0 uL/min
Oven temp.: 10° C.

Detector: UV, 245 nm wavelength
Inlector vol.: 5 μL
Stop time: 10 minutes
Retention times:
(S)-isocyanate: 6.2 minutes
(R)-isocyanate (IV): 6.9 minutes

EXAMPLE 5

[S-(R*,S*)]-N-[1,3-benzodioxol-5-yl)butyl]-3,3-diethyl-2-[-4-[(4-methyl-1-piperazinyl)carbonyl]phenoxy]-4-oxo-1-azetidinecarboxamide (I)

Toluene (212 kg) was charged to the reaction vessel and the stirred mixture was chilled to about 5° C., followed by the addition of 40.2 kg (113.0 moles active content) of (S) β-lactam (IV-b). A Karl-Fischer determination of the supernatant solution showed a water content of 440 ppm. To reduce the water content to 350 ppm or less, 42 kg of toluene was added and 13 kg of toluene distilled to reduce the water level to 42 ppm. A toluene solution of (R)-isocyanate (VI) (152.7 kg of a 17.1% w/w solution, 119 moles active content, water level determined to be 20 ppm) was added and the reaction slurry was cooled to −10° C. The catalyst (4.1 kg of a 1M solution of lithium tert-butoxide in hexane, 5.9 moles, 5.3 mol % relative to (S) β-lactam (IV-b)) was added at −10° C. A modest exotherm was observed during which the temperature of the reaction mass approached −5° C. over 6 minutes (the jacket temperature was held constant at −15° C. during the addition). All of the (S) β-lactam substrate dissolved within 30 minutes to give a light yellow solution. HPLC analysis showed the reaction was complete. The reaction was quenched with 0.41 kg of glacial acetic acid (6.8 mol) and washed with 43 kg of 2% aqueous sodium chloride solution while warming to 20° C. After separation of the aqueous layer, the reaction was concentrated to slightly less than one-half the original volume (from about 15% w/w content (I) to 30–32%) by distilling at 40° C./60 mm pressure to a volume of approximately 200 L (distillate weight of 200 kg). Analysis of the toluene solution by HPLC showed <0.1% area response for (R)-isocyanate 0.6% area response for (S) β-lactam (IV-b) and 0.19% area response for a symmetrical urea impurity. The warm, (40–45° C.) toluene solution was filtered through a 0.5μ, in-line cartridge filter into a 200 gallon, glass-lined vessel. After warming to 50° C., 58 kg of tert-butyl methyl ether was added, followed by 119 kg of heptanes (added over 1 hour while keeping the temperature at about 50° C.). The product precipitated during the heptanes addition and was held at 45° C. for one hour, then cooled at a constant rate to −15° C. over 7 hours. The reaction was centrifuged in four drops, and the cakes were washed with a total of 33 kg/61 kg of toluene/heptane which was precooled −20° C. The wet cake was dried to a constant weight in a vacuum tray oven at 40° C. and 50 mm to give 59.6 kg of white solid (I) (purity assayed by HPLC at 100% w/w) representing a corrected yield of 93%.

EXAMPLE 6

[S-(R*,S*)]-N-[1,3-benzodioxol-5-yl)butyl]-3,3-diethyl-2-[-4-[(4-methyl-1-piperazinyl)carbonyl]phenoxy]-4-oxo-1-azetidinecarboxamide (I)

A solution of (S) β-lactam (IV-b) (1 mmol, 0.345 g) and isocyanate (VI) (1 mmol, 200 μL) in 3.5 mL of tetrahydrofuran was cooled to −40° C. with stirring. sec-Butyl magnesium chloride (100 μL of a 2M solution) was added to the cooled solution via syringe. The reaction was stirred at this reduced temperature for approximately 20 minutes. An aliquot of the reaction mixture was subjected to HPLC analysis after being quenched with acidic eluent. The resulting chromatogram showed approximately 1.0% area response for (R)-isocyanate, <0.5% area response for (S) β-lactam (IV-b), 95.7% area response for compound (I), and 0.62% area response corresponding to the undesired (I) diastereomer.

EXAMPLE 7

[S-(R*,S*)]-N-[1,3-benzodioxol-5-yl)butyl]-3,3-diethyl-2-[-4-[(4-methyl-1-piperazinyl)carbonyl]phenoxy]-4-oxo-1-azetidinecarboxamide (I)

A solution of (S) β-lactam (IV-b) (1 mmol, 0.345 g) in 3.5 mL of tetrahydrofuran was cooled to −70° C. with stirring. To this solution was added tert-Butyl lithium in pentane (50 μL of a 1M solution) via syringe. The reaction was allowed to warm to −10° C., after which isocyanate (VI) (1 mmol, 200 μL) was added via syringe. The reaction was stirred for 15 minutes and total consumption of starting material was evident by HPLC analysis. The resulting chromatogram showed approximately 0.77% area response for (R)-isocyanate (VI), 0% area response for (S) β-lactam (IV-b), 96.8% area response for compound (I), and 0.65% area response corresponding to the undesired (I) diastereomer.

In Process HPLC Method

Column: Zorbax SB C18, 25 cm×4.6 mm
Temperature: 50° C.
Detector: 235 nm,
Flow: 1.1 mL/minute
Mobile Phase:
A=30% methanol/water (0.02 M in trifluoroacetic acid and triethylamine; pH 7.4)
B=acetonitrile
Gradient: 30% B to 70% B in a linear gradient over 15 minutes. After 15 minutes change the flow rate was adjusted to 1.5 mL/minute and a linear gradient to 95% B in 19 minutes was applied.
Stop time: 20 minutes
Retention times:
(S)-β-lactam (IV-b): 5.2 minutes
(R)-isocyanate (VI): 11.7 minutes
(I): 14.9 minutes

What is claimed is:
1. A process for the preparation of a compound of formula (IV):

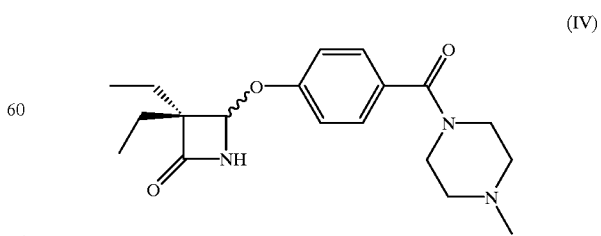

or a salt form thereof;

the process comprising:

(a) contacting a compound of formula (II):

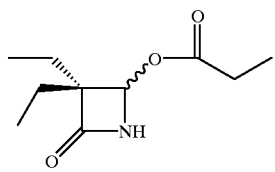
(II)

with a compound of formula (III):

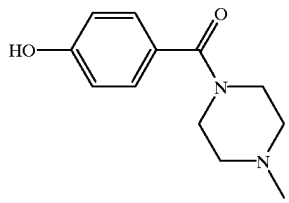
(III)

in a first polar solvent system in the presence of an aqueous base and a phase transfer catalyst, to form a compound of formula (IV), or a salt form thereof.

2. The process of claim 1, wherein:

the first polar solvent system comprises a mixture of water and a cosolvent selected from:
isopropyl acetate, methyl acetate, ethyl acetate, tert-butyl acetate, toluene, and tert-butyl methyl ether;

the aqueous base is selected from:
lithium carbonate, sodium carbonate, potassium carbonate, and cesium carbonate; and the phase transfer catalyst is selected from:
tetrabutylammonium bromide, tetrabutylammonium iodide, tetrabutylammonium hydrogen sulfate, and tetrabutylammonium chloride.

3. A process for the preparation of a compound of formula (IV-b):

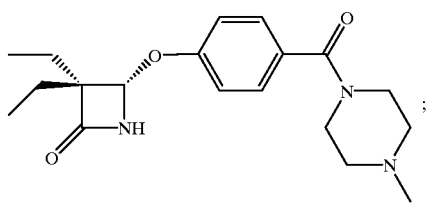
(IV-b)

the process comprising:

(b) contacting a compound of formula (IV):

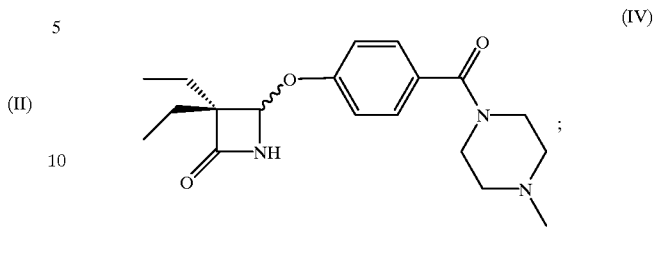
(IV)

with 2,3:4,6-Di-O-isopropylidene-2-keto-L-gulonic acid in a suitable solvent to form a precipitate of a compound of formula (IV-a):

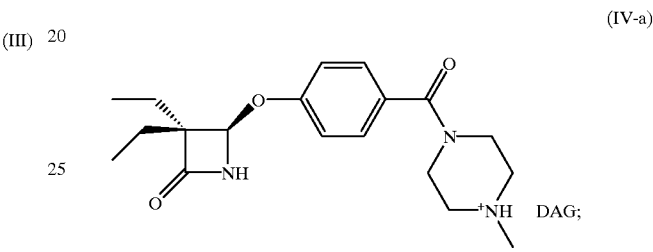
(IV-a)

and a mother liquor containing the compound of formula (IV-b);

(c) isolating the mother liquor; and (d) contacting the mother liquor with an antisolvent to precipitate a compound of formula (IV-b) as a crystalline solid.

4. The process of claim 3, further comprising:

(d-i) free basing and racemizing the compound formula (IV-a) to form a compound of formula (IV);

(d-ii) contacting the compound of formula (IV) formed in (d-i) with 2,3:4,6-Di-O-isopropylidene-2-keto-L-gulonic acid in a second suitable solvent to precipitate a second crop of a compound of formula (IV-a), and a second mother liquor containing a compound of formula (IV-b);

(d-iii) isolating the second mother liquor; and (d-iv) contacting the second mother liquor with a second antisolvent to precipitate a second crop of a compound of formula (IV-b) as a crystalline solid.

5. The process of claim 4, wherein free-basing and racemizing the compound of formula (IV-a) comprises contacting the compound of formula (IV-a) with an aqueous base in a polar solvent system comprising an aqueous phase and a cosolvent, in the presence of a phase transfer catalyst.

6. The process of claim 5, wherein:

the aqueous base is selected from:
lithium carbonate, sodium carbonate, potassium carbonate, and cesium carbonate;

the cosolvent selected from:
ethyl acetate, toluene, acetonitrile, isopropyl acetate, and methyl acetate; and the phase transfer catalyst is selected from:
tetrabutylammonium bromide, tetrabutylammonium chloride, tetrabutylammonium iodide, and tetrabutylammonium hydrogen sulfate.

7. The process of claim 5, further comprising:
(d-v) isolating the aqueous phase;
(d-vi) precipitating 2,3:4,6-Di-O-isopropylidene-2-L-gulonic acid monohydrate by contacting the aqueous phase with an aqueous acid; and
(d-vii) isolating the 2,3:4,6-Di-O-isopropylidene-2-L-gulonic acid monohydrate.

8. The process of claim 3, further comprising:
(e) contacting the compound of formula (IV-b) with a compound of formula (VI):

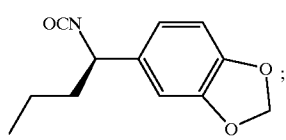

(VI)

in a coupling solvent, in the presence of a catalytic amount of a strong base to form a compound of formula (I):

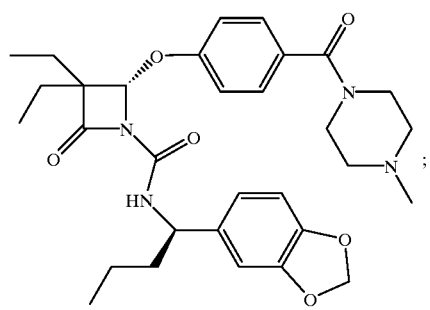

(I)

or a pharmaceutically acceptable salt form thereof.

9. The process of claim 8, wherein the compound of formula (VI) is prepared by the process comprising contacting a compound of formula (V):

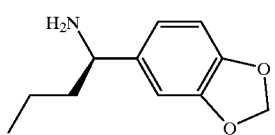

(V)

or a salt form thereof, with phosgene or a phosgene equivalent, in a second suitable solvent, at a suitable temperature in the presence of a catalytic amount of a complexing agent.

10. The process of claim 9, wherein:
the second suitable solvent is selected from:
toluene, o-xylene, m-xylene, p-xylene, and chlorobenzene;
the suitable temperature is about 80° C. to about 135° C.;
the catalytic amount of a completing agent is about 1 mole percent to about 10 mole percent; and the complexing agent is selected from:
lutidine, picoline, 1,10 phenanthroline, and pyridine.

11. A process for the formation of a compound of formula (I):

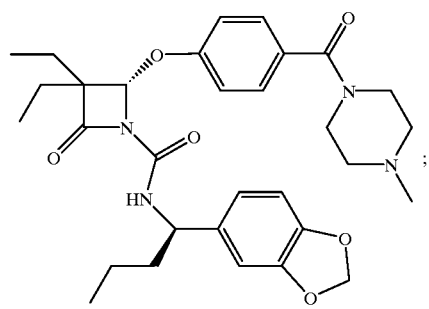

(I)

the process comprising:
(e) contacting a compound of (IV-b):

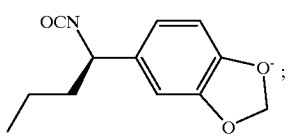

(IV-b)

with a compound of formula (VI):

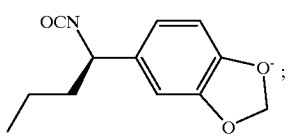

(VI)

in a coupling solvent, in the presence of a catalytic amount of a strong base to form a compound of formula (I), or a pharmaceutically acceptable salt form thereof.

12. The process of claim 11, wherein:
the strong base is selected from:
lithium tert-butoxide, potassium tert-butoxide, sodium tert-butoxide, sodium hydride, potassium hydride, tert-butyl lithium, butyl lithium, and sec-butyl magnesium bromide, and sec-butyl magnesium chloride;
the catalytic amount of strong base is about 1 mole percent to about 10 mole percent; and
the coupling solvent is selected from:
o-xylene, m-xylene, p-xylene, toluene, acetonitrile, and tert-butyl methyl ether.

* * * * *